United States Patent

Kasting, Jr. et al.

[11] Patent Number: 5,368,815
[45] Date of Patent: Nov. 29, 1994

[54] PROCESS AND APPARATUS FOR SANITIZING ARTICLES

[75] Inventors: John R. Kasting, Jr., Waxhaw; Ronald G. Potter, Monroe, both of N.C.; Michael P. Phillips, Rock Hill, S.C.

[73] Assignee: OxiDyn, Incorporated, Monroe, N.C.

[21] Appl. No.: 986,055

[22] Filed: Dec. 7, 1992

[51] Int. Cl.$^5$ .............................. A61L 2/24
[52] U.S. Cl. ........................ 422/3; 422/31; 422/115; 422/186.14; 422/302
[58] Field of Search ............... 210/96.1, 167, 192, 210/198, 739, 746, 748, 805, 85; 422/24, 28, 29, 31, 105, 108, 110, 115, 186.07, 186.08, 186.09, 186.14, 3, 302, 303, 304; 134/10, 11, 18, 56 R, 57 R, 109, 111; 137/1, 2, 87, 93

[56] References Cited

U.S. PATENT DOCUMENTS

| | | | |
|---|---|---|---|
| 3,024,138 | 3/1962 | Schlott | 134/1 |
| 3,302,655 | 2/1967 | Sasaki et al. | 422/186.04 |
| 3,313,311 | 12/1964 | Breeding et al. | 134/109 |
| 3,476,600 | 11/1969 | Morgan, Jr. et al. | 134/10 |
| 3,490,467 | 1/1970 | Gore et al. | 134/18 |
| 3,796,925 | 3/1974 | Breeding | 317/157 |
| 3,896,827 | 7/1975 | Robinson | 134/10 |
| 4,280,520 | 7/1981 | Fraula et al. | 134/60 |
| 4,313,767 | 2/1982 | Bemis et al. | 134/1 |
| 4,409,188 | 10/1983 | Silberzahn | 422/28 |
| 4,434,069 | 2/1984 | Fairchild | 252/174.14 |
| 4,505,836 | 3/1985 | Fairchild | 134/22.17 |
| 4,795,497 | 1/1989 | McConnell et al. | 134/902 |
| 5,082,558 | 1/1992 | Burris | 210/167 |
| 5,106,495 | 4/1992 | Hughes | 210/192 |

FOREIGN PATENT DOCUMENTS 3440315  5/1986  Germany ............... 422/186.07

Primary Examiner—Joseph W. Drodge
Attorney, Agent, or Firm—Bell, Seltzer, Park & Gibson

[57] ABSTRACT

An apparatus and process for supplying ozonated rinse water in a closed loop recirculating system to a rinsing apparatus for articles is described. The apparatus provides a pressure differential bypass line for providing a constant recirculating flow of ozonated water from a venturi directly to a water storage tank, bypassing the rinsing apparatus. Also included are a supply line to the rinsing apparatus and a diverted supply line for diverting flow back to the storage tank and bypassing the rinsing apparatus. The supply line and the diverted supply line have a normally closed solenoid valve and a normally open solenoid valve, respectively, for controlling the flow of ozonated water between them and maintaining and regulating pressure and volume of water for optimizing injection of ozone into the water and for maintaining ozone in the water.

23 Claims, 3 Drawing Sheets

PROCESS AND APPARATUS FOR SANITIZING ARTICLES

FIELD OF THE INVENTION

This invention relates to a process and apparatus for sanitizing articles. In particular, the invention claimed herein relates to the use of ozonated water to sanitize articles.

BACKGROUND OF THE INVENTION

Manufacturers of food products and beverages for human consumption typically package the beverage or food product. A variety of substances may be used to provide packaging for the products, including, but not limited to, plastics and glass. As a specific example, soft drinks typically are packaged in bottles formed from polyethylene terephthalate, otherwise known as "PET bottles." However, other plastics are also well known to the beverage and food packaging industries for use as containers for food and beverage products.

Current practice in the industry, and in particular for the packaging of soft drinks, is to rinse PET bottles with municipal water prior to filling the bottle with a soft drink. The use of hot water or chemical disinfectants typically has not been considered suitable for rinsing PET bottles prior to filling because hot water or disinfectants could chemically or physically alter the characteristics of a PET bottle. Such alterations could render the bottles unsuitable for containing beverages, or adversely affect the quality or taste of the beverage, or render the beverage unsuitable for human consumption.

Various devices and processes have been proposed for sanitizing containers such as bottles by contact with an ozonated rinse water. Ozone is highly reactive and is an effective oxidizing agent for sanitizing containers. Ozonated rinse water has the advantage over untreated rinse water of effectively removing microbes and other contaminants without changing the chemical or physical nature of the container. For example, Silberzahn U.S. Pat. No. 4,409,188 proposes a device for sterilizing containers that comprises a rotatable immersion wheel for immersing the containers in a bath of ozone and water. Numerous other devices using ozone as a sanitizing agent have also been proposed.

Hughes U.S. Pat. No. 5,106,495 proposes a portable water purification device that uses ozone as a treatment agent. Water in a tank is circulated by a pump through a venturi where ozone is injected into the water, which is then returned to the tank.

Burris U.S. Pat. No. 5,082,558 proposes a contact lens purification system in which sensors detect the concentration of ozone in the treatment liquid, and a controller acts responsibly to the sensor to control the residence time of the lenses in the system in response to the concentration of ozone.

McConnell et al. U.S. Pat. No. 4,795,497 proposes a method and a system for the fluid treatment of semiconductor wafers in a sequence of fluids and uses a closed fluid recirculation loop and a means for holding the wafers in the fluid flow path. In one embodiment, ozone is bubbled through the treatment fluid to enhance cleaning.

In spite of these previous devices and methods for using ozone as a sterilizing or cleaning agent, the food and beverage industry, and in particular the soft drink industry, still relies on municipal water supplies for rinsing PET containers prior to filling with soft drink. The rinse water typically is not recirculated, resulting in the run off of thousands of gallons of waste water and the high costs of operation associated with such a great use of municipal water supplies.

It would be desirable to develop an apparatus and process for sanitizing articles for food grade products, and in particular for plastic containers such as PET bottles for soft drinks, that could provide an automated recirculating operation of a captive and ozonated water supply. Such an apparatus and method could be effective to remove microbiological contaminants from food grade containers prior to filling with beverages or other food products without adversely affecting either the physical or chemical nature of the container. Additionally, by using a captive water supply, such an apparatus and process could save thousands of gallons of water, resulting in a substantial savings of money.

SUMMARY OF THE INVENTION

The invention claimed herein relates to a self-contained, automated apparatus and method for sanitizing articles such as PET bottles for soft drinks with a recirculated and ozonated water supply. Specifically, the apparatus provides a closed recirculation loop from an ozonated water supply to the articles for sanitizing, and return. A bypass recirculating means is provided so that after injection of ozone into the water, a predetermined portion of the ozonated water is continuously recirculated to the storage vessel through the bypass.

The remainder of the ozonated water is either supplied to the apparatus for contacting containers with the ozonated water and then returned to the storage vessel, or diverted through the bypass for return to the storage vessel in addition to the first predetermined portion, bypassing articles for sanitation. In this manner, ozonated water is continually supplied to the storage vessel and the pressure and volume of water is controlled for injecting ozone into the water and for maintaining ozone in the water sufficient for sanitation.

In a particular embodiment, the apparatus of the invention comprises a storage vessel for supplying ozonated water for sanitation of articles. This apparatus includes a means for injecting ozone into the water sufficient for sanitizing the articles. A first fluid flow conduit interconnects the storage vessel for ozonated water and the ozone injecting means. A second fluid flow conduit supplies ozonated water from the ozone injecting means to articles for sanitizing. A third fluid flow conduit returns water from the articles to the storage vessel, whereby the first, second, and third conduits form a closed recirculating loop system with the storage vessel when the apparatus is interconnected with and supplies ozonated water to an apparatus for contacting ozonated water with articles to be sanitized. A means is included providing for bypass recirculation of ozonated water from the ozone injecting means directly to the storage vessel, bypassing articles for sanitizing. This means controls the bypass recirculation between a predetermined first limit and a predetermined second limit in dependence on whether ozonated water is being supplied to articles for sanitizing or not.

In a more specific embodiment, the means for providing bypass recirculation of ozonated water comprises fourth and fifth fluid flow conduits and associated valves for automatically controlling fluid flow. In particular, the fourth fluid flow conduit interconnects the ozone injecting means and the storage vessel for ozonated water and supplies a recirculating bypass flow to the storage vessel at the predetermined first limit. The fifth fluid flow conduit also interconnects the ozone injecting means and the storage vessel for ozonated water. The fifth fluid flow conduit includes a first, normally open solenoid valve for supplying ozonated water to the vessel in combination with the fourth conduit at the predetermined second limit. Thereby, when the first solenoid is in a closed position, bypass recirculation is limited to the predetermined first limit through the fourth conduit.

The second conduit, which supplies ozonated water to articles for sanitation, includes a second normally closed solenoid valve that cooperates with the first, normally open solenoid valve. The first normally open solenoid valve diverts ozonated water to the storage vessel through the fifth conduit when the first valve is open and the second valve is closed. When the second valve is open and the first valve is closed, then ozonated water is supplied through the second conduit to articles for sanitizing. In this manner, the supply of ozonated water to articles for sanitizing is controlled, the pressure and volume of water are controlled for injecting ozone into the water and maintaining ozone in the water sufficient for sanitizing articles, and the bypass recirculation is controlled between the predetermined first and second limits.

In still more specific embodiments, one or more redox probes are provided for insertion into a pair of ports in the fluid conduits for determining 1) the concentration of ozone in the water prior to contact with articles for sanitation, and 2) after contact with articles for sanitation. An electrical system is provided for controlling the solenoid valves and the container conveyor in response to the ozone concentrations in the rinse water as measured by the redox probe.

The invention also includes a process for sanitizing articles with ozonated water wherein the process is characterized by automatic recirculating flow of a captive water supply. The process comprises supplying water from a source for ozonation, injecting ozone into the water and returning at least a predetermined first portion of the ozonated water to the source. A predetermined second portion of the ozonated water is alternately supplied to the articles for sanitizing or returned to the source, bypassing the articles for sanitizing. When the predetermined second portion of ozonated water is supplied to articles for sanitizing, then the used ozonated water is also returned to the storage vessel.

In a more specific embodiment, the process includes the steps of establishing a set point for a minimum concentration of ozone in the water, monitoring the concentration of ozone in the water prior to supplying ozonated water to the articles for sanitizing, and supplying ozonated water to the articles when the monitored concentration of the ozone in the water is above the minimum.

In another specific embodiment, the process comprises the steps of establishing a set point for a maximum loss of ozone concentration over time, monitoring the concentration of ozone in the water with respect to time after supplying ozonated water to articles for sanitizing, and ceasing to supply ozonated water to the articles when the monitored concentration of ozone exceeds the set point for a maximum loss over time. In this manner, if a contaminant, such as a hydrocarbon contaminant, causes the ozone level to drop very quickly, then the sanitizing process can be halted until the condition is corrected. However, minor or slow fluctuations in the ozone level need not interrupt the process.

DETAILED DESCRIPTION OF THE PREFERRED EMBODIMENTS

Figure 1:
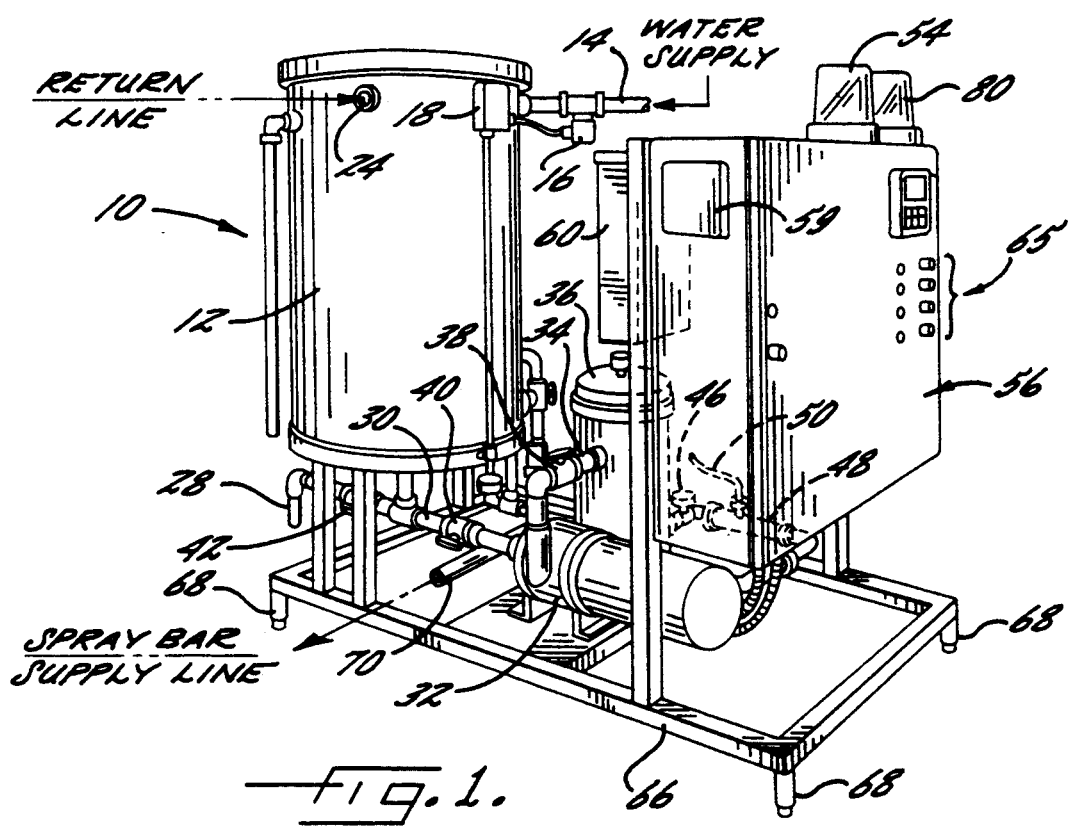
FIG. 1 is a prospective view of a preferred embodiment of the apparatus of the invention.

FIG. 1 shows broadly at 10 a perspective view of a preferred embodiment of the apparatus of the invention. The apparatus includes a storage vessel for supplying ozonated water for sanitation of articles, storage tank in which an ozonated water supply is stored and maintained. The storage tank and other components of the apparatus that come into contact with ozonated water should be constructed of materials that are resistant to oxidation, such as polyethylene, polyvinylchloride, or, most preferred for rigid bodies, stainless steel. However, additional plastics and some other materials will also be suitable for use in practice of the present invention, as will be recognized by the skilled artisan.

Figure 2:
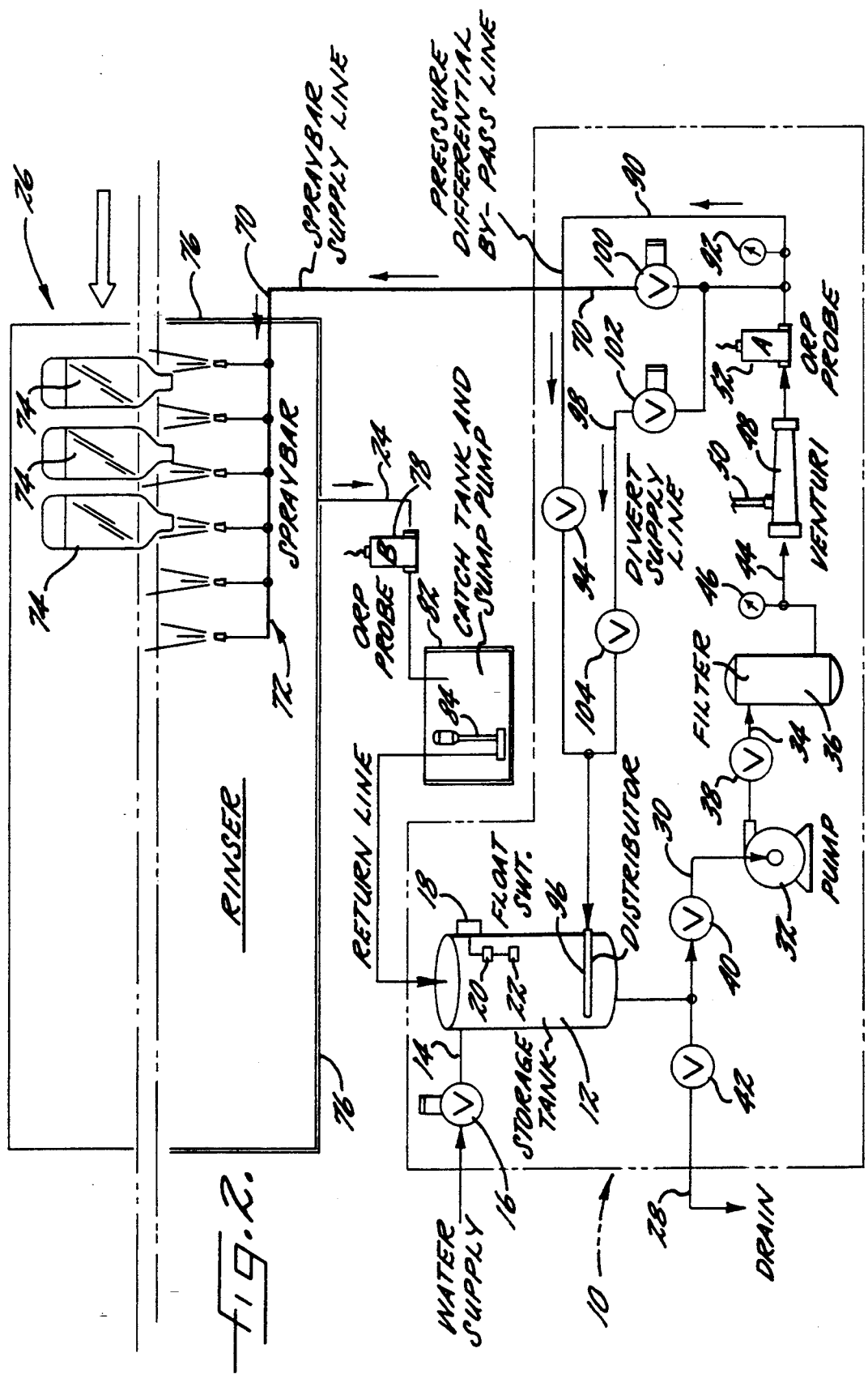
FIG. 2 is a highly schematic flow diagram showing interconnection of the apparatus of FIG. 1 with a device for contacting PET soft drink bottles with ozonated rinse water.

Storage tank 12 includes a water supply 14 by which the storage tank is filled with water initially and through which make up water can be added as needed. A suitable electrical control, solenoid valve 16, is provided on the water supply conduit for automatic on/off operation of the water supply line. The solenoid valve is connected to a float switch 18 (FIG. 2). Float switch 18 monitors the level of water in the tank 12 and indicates when the tank 12 is full and when water should be added to the tank to maintain a minimum level. Preferably, the float switch is a stainless steel dual float assembly providing for high and low water levels 20 and 22 respectively. Additionally, a secondary timing device is preferably included to automatically displace any excess heat built up in the storage tank.

A return line 24 is also provided on the storage tank for return of ozonated rinse water from a PET bottle rinser 26 (FIG. 2). Also shown in FIG. 1, is a drain line 28 from the storage tank through which the tank may be emptied of water. Rinse water is supplied from the storage tank for injection of ozone through conduit 30.

Water in conduit 30 is supplied from the storage tank to a pump 32. Pump 30 provides a means for circulating fluid throughout the system. The pump components for contact with ozonated water should be made of a material resistant to oxidation, preferably stainless steel. The skilled artisan will recognize that the pump should be selected and sized based on the volume of fluid to be transported through the system. Water exits the pump through a conduit 34 and enters a particulate filter 36 for removal of solid contaminants that may enter the fluid circulating lines through the rinsing process. The particulate filter housing and filtration components should be constructed of materials resistant to oxidation by ozone, as will be recognized by the skilled artisan.

A valve 38 is included on fluid flow line 34 by which flow to filter 36 may be regulated. Valve 38 is a ball valve and will be used primarily for isolating components of the system, such as the filter, should it become necessary to change the filter elements. The skilled artisan will recognize that other types of valves may be selected. A similar valve 40 is included on conduit 30 from the storage tank to the pump. Together, valves 40 and 38 provide a convenient method for isolating the pump should it become necessary to perform maintenance procedures on the pump or to remove the pump from the system. Also, a similar valve 42 is included on conduit 28 for controlling flow of fluid from the storage tank through the drain line 28.

After exiting filter 36, the fluid enters a conduit 44 shown in FIG. 1 in shadow behind additional components to be discussed hereinbelow. A pressure gauge 46 is shown on line 44 just prior to ozone injecting means, venturi 48. Ozone containing gas is supplied to venturi 48 through a gas line 50 for injection into the water as it passes through the venturi. A venturi provides a short section of a gradually tapering, more constricted flow path for the fluid in the pipe that results in an increase in the velocity of the fluid and a corresponding reduction in fluid pressure. Together, fluid flow conduits 30, 34, and 44 form a first fluid flow conduit interconnecting the storage tank 12 and the venturi 48. The skilled artisan will recognize that the venturi should be made from materials suitable for use in a system for supplying rinse water to packaging for food grade products.

Figure 3:
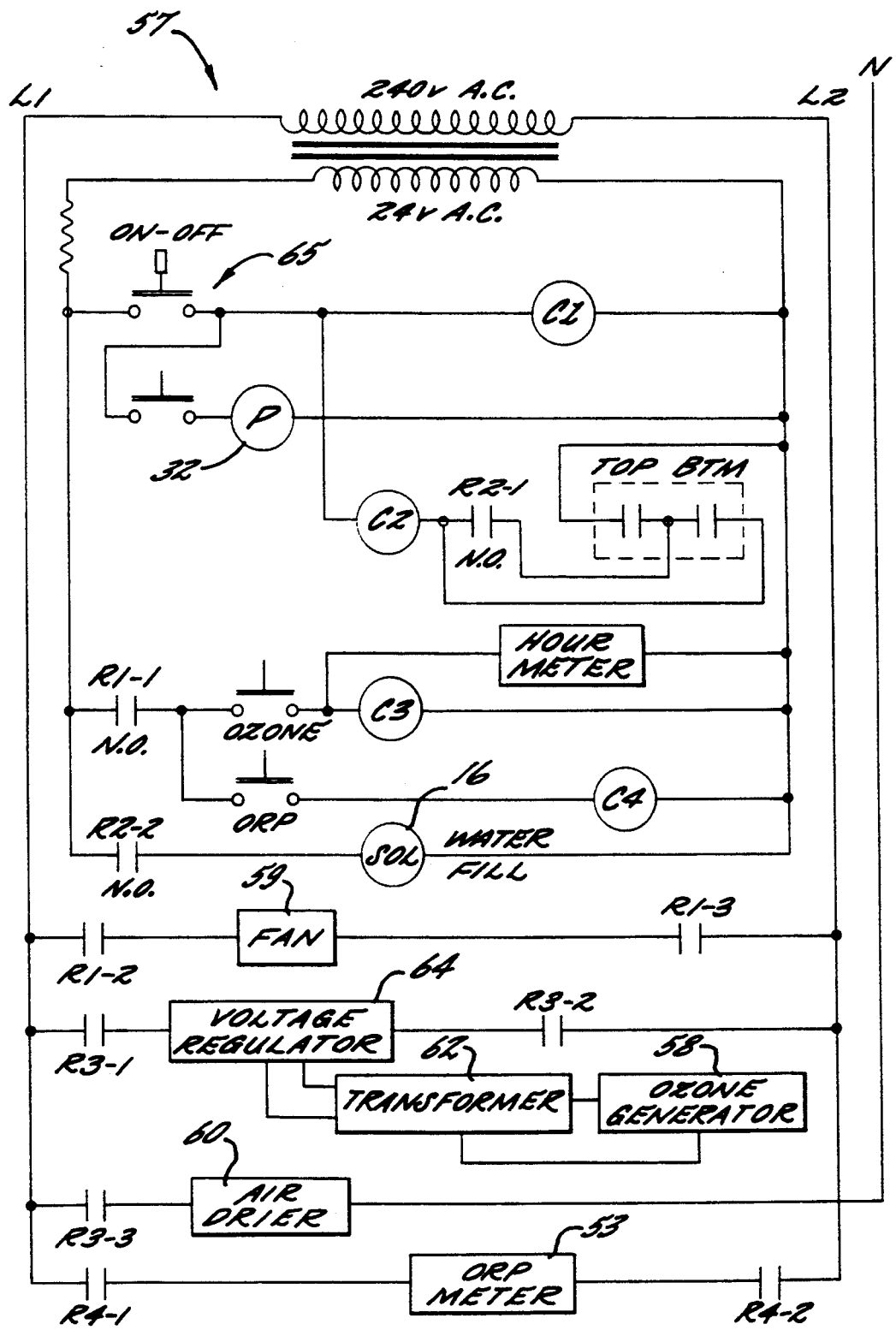
FIG. 3 is a simplified and highly schematic diagram of the electrical components of the apparatus as illustrated in FIG. 1.

Ozonated water is then conveyed from the venturi through an ORP probe (redox, or Oxidation Reduction Probe) 52 (FIG. 2) which is inserted into an access port in the conduit and monitors the level of ozone in the rinse water. The ORP probe 52 provides an output relay to an ORP meter 53 (FIG. 3) depending on a set point for a low level of ozone concentration. The output relay can be used to initiate a warning light 54 (FIG. 1) or can be connected directly to the rinser to shut down operation of the rinser in the event of a low ozone concentration.

The ozone generating system for supplying ozone containing gas to the venturi 48 for injection into the water is contained within housing 56 illustrated in FIG. 1. The components of the ozone generating system are illustrated schematically in the simplified electrical diagram of FIG. 3 at 57. An ozone generator 58 generates ozone from dry compressed air and supplies ozone containing air to venturi 48. Preferably, ozone generator 58 should comprise a mercury free corona lamp spaced from a stainless steel chamber having internal and external flow passages for dry air for ozone generation and to provide adequate cooling capacity for the chambers of the ozone generator. A corona lamp for an ozone generator of this description is available from LCD Lighting, Inc., 11 Cascade Boulevard, Milford, Conn. 06460-0870. Multiple corona tubes with stainless steel jackets can be incorporated in parallel into a single generator for greater ozone producing capacity. A fan 59 is used to supply air to the interior of housing 56 to provide cooling for the equipment.

Air to be supplied to the ozone generator should be dry. A suitable air dryer 60 (FIGS. 1 and 3) for use in connection with the practice of the invention claimed herein is available from Domnick Hunter, Inc., having worldwide offices and an office at 6636-D East W. T. Harris Boulevard, Charlotte, N.C. 28215. Specifically, Domnick Hunter merchandises a self-regenerating air dryer having a $-100°$ degree Fahrenheit dew point. The desiccant is a nitrogen-reducing mixed bed type. The air dryer includes filters prior to and after the desiccant with 0.01 micron filter elements and a water separator. This air dryer is self-regenerating and has a timer circuitry. Air is supplied to the air drier using any suitable compression means, as will be known to the skilled artisan.

Power is supplied to the ozone generator by a transformer 62. Power is supplied to the air dryer and other components as line voltage. It is preferable in the practice of the invention claimed herein to use an inductive, step-up high voltage transformer. Preferably, this high voltage transformer will have a 240 VAC 50/60 cycle primary and a 9,000 volt secondary for operating corona lamps in parallel; although other values may be selected depending on need. A suitable transformer is available from Magnetics and Controls, Inc., Rosemont, N.J. 08556.

A voltage regulator 64 should be used to provide a stable and consistent voltage for the ozone generator and the ORP meters. Power is supplied to the various components by a series of on/off switches 65 on housing 56.

As illustrated FIG. 1, the entire unit 10 is portable and mounted on a stand 66 having adjustable legs 68. The entire unit can be conveniently moved for attachment to an apparatus for supplying ozonated water for contact with articles to be sanitized and for return of water to the storage tank 12. Although a PET bottle rinsing apparatus such as that used in the soft drink industry is illustrated, the skilled artisan will recognize that the apparatus of FIG. 1 could be interconnected with any number of apparatus for supplying ozonated rinse water for sanitation. For example, the apparatus of FIG. 10 could be connected to a rinser for sanitizing crates for carrying individual food containers (case washer).

FIG. 2 illustrates a highly schematic flow diagram of the apparatus 10 of FIG. 1 interconnected with a spray bar supply line 70 for supplying ozonated water to a spray bar 72 for spraying PET soft drink bottles 74. Spray bar 72 is located in a rinser shown broadly at 26. PET bottles are advanced in the direction of the arrow through the rinser where the PET bottles are contacted with a spray of ozonated water from the spray bar 72. Rinser 26 provides a collecting pan 76 by which the rinse water is collected after being sprayed on the bottles. A return line 24 conveys the used rinse water from the collecting pan to the storage tank 12. A second ORP probe (redox or Oxidation Reduction Probe) 78 is included in an access port in return line 24. As will be recognized by the skilled artisan, a single ORP probe can be used to access both the ports at each location shown in FIG. 2 as ORP probe 52 and ORP probe 78. If more than one ORP probe is used, then it shall be necessary to use two ORP meters. ORP probe 78 provides a relay to an ORP meter such as at 53 (FIG. 3) in the event that ozone concentration drops below a predetermined level within a predetermined short period of time. For example, the meter can be set to respond if the ORP probe shows a 20 mV drop in 3 seconds. If the ozone level drops too fast, then a contaminant situation is indicated, such as a hydrocarbon, that would necessitate stopping the rinser, either by stopping conveyance of the bottles through the rinser or by stopping the flow of ozonated water. The ORP probe 78 can provide a relay to initiate a warning signal via a lamp 80 (FIG. 1) or to stop the rinser operation. ORP probe 78 thereby provides an in-line contaminant detection sensing capability.

A catch tank 82 and sump pump 84 are also included in return line 24 for providing flow of collected and used rinse water to the storage tank 12. Together, fluid flow conduits 30, 34, 44, which constitute a first fluid flow conduit from the storage tank to the venturi; second fluid flow conduit 70; and third fluid flow conduit 24 provide a closed loop recirculating system for conveyance and return of a captive ozonated water supply.

In addition to the storage tank 12, the pump 32, the filter 36, the venturi 48, and associated flow lines discussed in connection with FIG. 1, FIG. 2 also illustrates a means for providing bypass recirculation of ozonated water from the venturi directly to the storage tank. Pressure differential bypass line 90 constitutes a fourth fluid flow conduit that along with associated pressure gauge 92 and metering valve 94 provide a constant recirculating flow of ozonated water from the venturi 48 to the storage tank 12. A distributor 96 is included in storage tank 12 for distributing the ozonated water via line 90 into the storage tank. Distributor 96 is preferably a manifold type with numerous orifices provided for bubbling the ozone containing water into the water contained in the storage tank. In this manner, a constant supply of freshly ozonated water is supplied to the water in the storage tank.

Additionally, a fifth fluid flow conduit, line 98 is provided for diverting the supply of ozonated water from spray bar supply line 70 back to the storage tank 12, bypassing spray bar 72. As illustrated, the diverted supply line 98 joins line 90 and enters distributor 96 for distributing freshly ozonated water into storage tank As will be recognized by the skilled artisan, supply line could be supplied as a separate line to storage tank 12.

Spray bar supply line 70 and diverted supply line 98 each include solenoid valves 100 and 102, respectively, for controlling the flow of ozonated water. Solenoid valve 100 is a normally closed solenoid that is open to supply ozonated water to the spray bar 72. Solenoid valve 102 in the diverted supply line is a normally open solenoid for diverting supply of ozonated water from supply line 70 to storage tank 12 via line 98. In this manner, a predetermined flow of ozonated water is recirculated through the system from the venturi 48 through the diverted supply line 98 to the storage tank 12 when solenoid 102 is in its normally opened position.

When operation of the rinser 26 is commenced, then normally opened solenoid 102 closes and normally closed solenoid 100 opens to supply a predetermined flow of ozonated water to the spray bar 72 for collection in collecting pan 76 and return via return line 24 to the storage tank 12. As can be seen, recirculating flow to the storage tank is maintained between a first limit, which corresponds to flow through line 90, and a second limit, which corresponds to the combined flows through line 90 and diverted supply line 98. Metering valves 94 in line 90 and 104 in line 98 are provided to throttle and regulate pressure and back pressure to optimize injection of ozone into the water at the venturi and to maintain ozone in the water as it is sprayed through the spray bar 72 onto bottles 74.

The invention claimed herein has been described with respect to specific embodiments illustrated in the drawings. However, the skilled artisan will recognize that variations can be made within the scope and spirit of the invention as described in the foregoing specification and defined in the appended claims. While the invention has been described with reference to preferred embodiments, it should be understood that the invention is not intended to be limited to the embodiments illustrated in the drawings, to the rinsing of PET bottles for the beverage industry, or to other specific rinsing systems. On the contrary, the invention includes all alternatives, modifications, and equivalents that may be included within the scope and spirit of the invention as defined by the appended claims.

That which is claimed is:

1. Apparatus adapted for supplying ozone-containing water for sanitizing articles, said apparatus being characterized by automatic recirculating operation of a captive water supply, said apparatus comprising:
   (a) a storage vessel arranged for supplying water to be ozonated for sanitation of articles;
   (b) means for injecting ozone into the supplied water sufficient for sanitizing articles:
   (c) a first fluid flow conduit in fluid flow communication at one end thereof with said storage vessel for ozonated water and in fluid flow communication at the other end thereof with said ozone injecting means;
   (d) a second fluid flow conduit in fluid flow communication at one end thereof with said ozone injecting means, the other end thereof arranged for providing ozonated water to means for contacting articles with ozonated water;
   (e) a third fluid flow conduit in fluid flow communication at one end thereof with said storage vessel, the other end thereof being arranged for receiving water from the means for contacting articles with ozonated water, whereby said first, second, and third conduits form a closed loop recirculating system with said storage vessel when said apparatus is interconnected with and supplies ozonated water to means for contacting articles to be sanitized with ozonated water;
   (f) means for providing bypass recirculation of ozonated water from said ozone injecting means directly to said storage vessel and bypassing the means for contacting articles with ozonated water; and
   (g) means for controlling said bypass recirculation providing means between predetermined first and second limits in dependence on concentration of ozone in the ozonated water, whereby ozonated water is continually supplied to said storage vessel and the pressure and volume of water are controlled for injecting ozone into the water and maintaining ozone in the water.

2. Apparatus according to claim 1 wherein said means for providing bypass recirculation of ozonated water comprises:
   (a) a fourth fluid flow conduit in fluid flow communication at one end thereof with said ozone injecting means and at the other end thereof with said storage vessel for ozonated water for supplying recirculating bypass flow to said vessel at the predetermined first limit;
   (b) a fifth fluid flow conduit in fluid flow communication at one end thereof with said ozone injecting means and at the other end thereof with said storage vessel for ozonated water;
   (c) a first, normally open valve cooperating with said fifth conduit for supplying ozonated water to said storage vessel in combination with said fourth conduit at the predetermined second limit, whereby when closed said first valve limits bypass recirculation to the predetermined first limit through said fourth conduit; and (d) a second, normally closed valve cooperating with said second conduit and said first, normally open valve for diverting ozonated water to said storage vessel through said fifth conduit when said first valve is open and said second valve is closed and, when said second valve is open and said first valve is closed, for supplying ozonated water through said second conduit to the means for contacting articles with ozonated water for sanitizing, whereby supply of ozonated water to articles for sanitizing is controlled, the pressure and volume of water are controlled for injecting ozone into the water and maintaining ozone in the water sufficient for sanitizing articles, and bypass recirculation is controlled between the predetermined first and second limits.

3. Apparatus of claim 2 wherein said first, normally open valve and said second, normally closed valve are solenoid valves and said apparatus further comprises means for monitoring the concentration of ozone in the ozonated water and means for electrically controlling said solenoid valves in response to the concentration of ozone in the ozonated water.

4. Apparatus of claim 2 wherein said fourth conduit includes a metering valve to control the flow of water through said fourth conduit at the predetermined first limit.

5. Apparatus of claim 1 further comprising means for monitoring the concentration of ozone in the ozonated water.

6. Apparatus of claim 5 wherein said means for monitoring the concentration of ozone in the ozonated water comprises:
   (a) a first redox probe located adjacent to and downstream of said ozone injecting means for generating a signal indicative of the concentration of ozone in the water in the second conduit; and
   (b) a second redox probe located in said third conduit for returning water to said vessel for generating a signal indicative of the concentration of ozone in the water in the third conduit.

7. Apparatus of claim 6 further comprising means for automatically responding to said signals and controlling said means for providing bypass recirculation.

8. Apparatus adapted for sanitizing PET bottles with ozone-containing water, said apparatus being characterized by automatic recirculating operation of a captive water supply, said apparatus comprising:
   (a) means for contacting PET bottles with ozonated water;
   (b) a storage vessel arranged for supplying water to be ozonated for sanitation of the bottles to said bottle contacting means;
   (c) means for injecting ozone into the supplied water sufficient for sanitizing the PET bottles, said means comprising an ozone generator, an air drier operatively connected to said generator for supplying dehumidified air to said generator, and a venturi operatively connected to said generator for injecting ozone containing air from said generator into water;
   (d) a first fluid flow conduit in fluid flow communication at one end thereof with said storage vessel for ozonated water and at the other end thereof with said venturi;
   (e) a second fluid flow conduit in fluid flow communication at one end thereof with said venturi and arranged at the other end thereof for conveying ozonated water from said venturi to said means for contacting PET bottles with ozonated water;
   (f) a third fluid flow conduit in fluid flow communication at one end thereof with said storage vessel and arranged at the other end thereof for receiving water from said bottle contacting means and returning the water to said storage vessel whereby said first, second, and third conduits form a closed loop recirculating system with said storage vessel and said bottle contacting means;
   (g) a fourth fluid flow conduit in fluid flow communication at one end thereof with said venturi and at the opposite end thereof with said storage vessel for ozonated water and arranged for supplying recirculating bypass flow to said vessel at a predetermined first limit;
   (h) a fifth fluid flow conduit in fluid flow communication at one end thereof with said venturi and at the other end thereof with said storage vessel for ozonated water;
   (i) a first, normally open solenoid valve cooperating with said fifth conduit and arranged for supplying ozonated water to said vessel in combination with said fourth conduit at a predetermined second limit, whereby when closed said first valve limits bypass recirculation to the predetermined first limit through said fourth conduit;
   (j) a second, normally closed solenoid valve cooperating with said second conduit and said first, normally open solenoid valve for diverting ozonated water to said vessel through said fifth conduit when said first valve is open and said second valve is closed and for supplying ozonated water to said bottle contacting means through said second conduit when said second valve is open and said first valve is closed, whereby the supply of ozonated water to said bottle contacting means is controlled, the pressure and volume of water are controlled for injecting ozone into the water and maintaining ozone in the water sufficient for sanitizing PET bottles, and bypass recirculation is controlled between the predetermined first and second limits; and
   (k) means for electrically controlling said solenoid valves in response to the concentration of ozone in the water.

9. Apparatus of claim 8 wherein said means for controlling the solenoid valves in response to the concentration of ozone in the water comprises:
   (a) a first redox probe located adjacent to and downstream of said ozone injecting means for generating a signal indicative of the concentration of ozone in the second conduit; and
   (b) a second redox probe located in said third conduit for returning water to said vessel for generating a signal indicative of the concentration of ozone in the third conduit.

10. A process for sanitizing articles with ozonated water, said process being characterized by automatic recirculating flow of a captive water supply, said process comprising the steps of:
   (a) supplying water from a source thereof for ozonation;
   (b) injecting ozone into the water for the ozonation;

(c) returning at least a predetermined first portion of the ozonated water to the source through means arranged for bypassing the articles;

(d) supplying a predetermined second portion of the ozonated water to the articles for sanitizing when the concentration of ozone in the ozonated water is sufficient for sanitizing articles; and (e) returning at least a substantial portion of the second portion of the ozonated water to the source.

11. The process of claim 10 further comprising the steps of:

(a) establishing a set point for a minimum concentration of ozone in the water;

(b) monitoring the concentration of ozone in the ozonated water prior to supplying ozonated water to the articles for sanitizing; and (c) supplying ozonated water to the articles when the monitored concentration of the ozone in the ozonated water is above the minimum.

12. The process of claim 11 wherein the step of supplying ozonated water to the articles is automatically controlled in response to the monitored concentration of ozone in the ozonated water.

13. The process of claim 11 further comprising the step of sensing when articles are present for sanitizing and supplying ozonated water to the articles when said articles are present.

14. The process of claim 10 further comprising the steps of:

(a) establishing a set point for maximum loss of ozone concentration over time;

(b) monitoring the concentration of ozone in the water being returned to the source with respect to time; and (c) ceasing to supply ozonated water to the articles when the monitored concentration of ozone in the water being returned to the source exceeds the set point for maximum ozone loss over time.

15. The process of claim 14 wherein the step of ceasing to supply ozonated water to the articles is automatically controlled in response to the monitored concentration of ozone in the water being returned to the source.

16. A process for sanitizing articles with ozonated water, said process being characterized by automatic recirculating flow of a captive water supply, said process comprising the steps of:

(a) supplying water from a source thereof for ozonation;

(b) injecting ozone into the supplied water for ozonation;

(c) returning at least a predetermined first portion of the ozonated water to the source;

(d) establishing a set point for a minimum concentration of ozone in the (e) monitoring the concentration of ozone in the water prior to supplying ozonated water to the articles for sanitizing;

(f) supplying a predetermined second portion of the ozonated water to the articles for sanitizing when the monitored concentration of the ozone in the water is above the minimum; and (g) returning the predetermined second portion of ozonated water to the source in combination with said first portion so that the second portion bypasses the articles when the monitored concentration of the ozone in the ozonated water is below the minimum.

17. A process for sanitizing articles with ozonated water, said process being characterized by automatic recirculating flow of a captive water supply, said process comprising the steps of:

(a) supplying water from a source thereof for ozonation;

(b) injecting ozone into the supplied water for ozonation;

(c) returning at least a predetermined first portion of the ozonated water to the source;

(d) supplying a predetermined second portion of the ozonated water to the articles for sanitizing:

(e) returning the second portion of ozonated water to the source;

(f) establishing a set point for maximum loss of ozone concentration over time;

(g) monitoring the concentration of ozone in the second portion of the water being returned to the source with respect to time;

(h) ceasing to supply ozonated water to the articles when the monitored concentration of ozone in the second portion of the water being returned to the source exceeds the set point for maximum ozone loss over time; and (i) returning the predetermined second portion of ozonated water to the source in combination with said first portion so that the second portion bypasses the articles when the supply of ozonated water to the articles is ceased.

18. Apparatus adapted for supplying ozone containing water for sanitizing articles, said apparatus being characterized by automatic recirculating operation of a captive water supply, said apparatus comprising:

(a) a storage vessel for supplying water to be ozonated for sanitation of articles;

(b) means for injecting ozone into the supplied water sufficient for sanitizing articles;

(c) a first fluid flow conduit in fluid flow communication at one end thereof with said storage vessel for ozonated water and at the other end thereof with said ozone injecting means;

(d) a second fluid flow conduit in fluid flow communication at one end thereof with said ozone injecting means and being arranged at the opposite end thereof for fluid flow communication with a means for contacting articles with ozonated water for sanitation;

(e) a third fluid flow conduit in fluid flow communication at one end thereof with said storage vessel and being arranged at the opposite end thereof for receiving water from the means for contacting articles with ozonated water for sanitation and returning the water to said storage vessel, whereby said first, second, and third conduits form a closed loop recirculating system with said storage vessel when said apparatus is interconnected with and supplies ozonated water to means for contacting articles to be sanitized with ozonated water;

(f) a fourth fluid flow conduit in fluid flow communication at one end thereof with said ozone injecting means and at the other end thereof with said storage vessel for ozonated water and arranged for supplying recirculating bypass flow to said storage vessel at a predetermined first limit;

(g) a fifth fluid flow conduit in fluid flow communication at one end thereof with said ozone injecting means and at the other end thereof with said storage vessel for ozonated water;

(h) a first, normally open valve cooperating with said fifth conduit and art arranged for supplying ozonated water to said vessel in combination with said fourth conduit at a predetermined second limit, whereby when closed said first valve limits bypass recirculation to the predetermined first limit through said fourth conduit; and (i) a second, normally closed valve cooperating with said second conduit and with said first, normally open valve for diverting ozonated water to said vessel through said fifth conduit when said first valve is open and said second valve is closed and for supplying ozonated water for sanitizing to the article contacting means through said second conduit when said second valve is open and said first valve is closed, whereby supply of ozonated water to articles for sanitizing is controlled, the pressure and volume of water are controlled for injecting ozone into the water and maintaining ozone in the water sufficient for sanitizing articles, and bypass recirculation is controlled between the predetermined first and second limits.

19. Apparatus of claim 18 wherein said first normally open valve and said second normally closed valve are solenoid valves and said apparatus further comprises means for monitoring the concentration of ozone in the ozonated water and means for electrically controlling said solenoid valves in response to the concentration of ozone in the ozonated water.

20. Apparatus of claim 18 wherein said fourth conduit includes a metering valve to control the flow of water through said fourth conduit at the predetermined first limit.

21. Apparatus of claim 18 further comprising means for monitoring the concentration of ozone in the ozonated water to determine whether to initiate or cease contacting articles with ozonated water.

22. Apparatus of claim 21 wherein said means for monitoring the concentration of ozone in the ozonated water comprises:

a) a first redox probe located adjacent to and downstream of said ozone injecting means for generating a signal indicative of the concentration of ozone in the ozonated water, whereby a determination can be made whether the concentration is sufficient to initiate contacting articles with water; and b) a second redox probe located in said third conduit arranged for returning water to said vessel for generating a signal indicative of the concentration of ozone in the water, whereby a determination can be made whether to cease contacting articles with water in the event the ozone level is suddenly depleted.

23. Apparatus adapted for supplying ozone-containing water for sanitizing articles, said apparatus being characterized by automatic recirculating operation of a captive water supply, said apparatus comprising:

(a) a storage vessel arranged for supplying water to be ozonated for sanitation of articles;

(b) means for injecting ozone into the supplied water sufficient for sanitizing articles;

(c) a first fluid flow conduit in fluid flow communication at one end thereof with said storage vessel for ozonated water and at the other end thereof with said ozone injecting means;

(d) a second fluid flow conduit in fluid flow communication at one end thereof with said ozone injecting means and being arranged at said other end for conveying ozonated water from said ozone injecting means to means for contacting articles to be sanitized with ozonated water;

(e) a third fluid flow conduit in fluid flow communication at one end thereof with said storage vessel and being arranged at the other end for receiving water from the means for contacting articles with ozonated water and returning the water to said storage vessel, whereby said first, second, and third conduits form a closed loop recirculating system with said vessel when said apparatus is interconnected with and supplies ozonated water to means for contacting articles with ozonated water;

(f) means for providing bypass recirculation of ozonated water from said ozone injecting means directly to said vessel and bypassing means for contacting articles with ozonated water for sanitizing, said means controlling bypass recirculation between predetermined first and second limits in dependence on whether ozonated water is being supplied to article contacting means, wherein ozonated water is continually supplied to said vessel and the pressure and volume of water are controlled for injecting ozone into the water and maintaining ozone in the water; and (g) means for monitoring the concentration of ozone in the ozonated water to determine whether to initiate or cease contacting articles with ozonated water, said means comprising a first redox probe located adjacent to and downstream of said ozone injecting means for generating a signal indicative of the concentration of ozone in the water, whereby a determination can be made whether the concentration is sufficient to initiate contacting articles with water and a second redox probe located in said third conduit arranged for returning water to said vessel for generating a signal indicative of the concentration of ozone in the water, whereby a determination can be made whether to cease contacting articles with water in the event the ozone level is suddenly depleted, and means for automatically responding to said signals and controlling said means for bypass recirculation.

* * * * *

UNITED STATES PATENT AND TRADEMARK OFFICE
CERTIFICATE OF CORRECTION

PATENT NO. : 5,368,815
DATED      : November 29, 1994
INVENTOR(S): Kasting, Jr. et al.

It is certified that error appears in the above-identified patent and that said Letters Patent is hereby corrected as shown below:

Column 4, line 20, after "tank", insert -- 12 --.

Column 7, line 31, after "tank", insert -- 12 --.

Column 7, line 32, after "line", insert -- 98 --.

Column 11, line 55, after "in the" insert -- ozonated water; --.

Column 13, line 2, delete "art".

Signed and Sealed this

Seventh Day of February, 1995

Attest:

BRUCE LEHMAN

Attesting Officer  Commissioner of Patents and Trademarks